United States Patent [19]

Panneman

[11] Patent Number: 4,499,105
[45] Date of Patent: Feb. 12, 1985

[54] CARBOXYIMIDAMIDE DERIVATIVES

[75] Inventor: Harm J. Panneman, Oss, Netherlands

[73] Assignee: Akzo N.V., Arnhem, Netherlands

[21] Appl. No.: 452,194

[22] Filed: Dec. 28, 1982

Related U.S. Application Data

[63] Continuation of Ser. No. 214,889, Dec. 9, 1980, abandoned.

[30] Foreign Application Priority Data

Dec. 12, 1979 [NL] Netherlands .......................... 7908922

[51] Int. Cl.³ .................. A61K 31/22; A61K 31/155; C07C 123/00
[52] U.S. Cl. ..................................... 514/631; 514/632; 514/633; 560/139; 564/80; 564/82; 564/226; 564/229; 564/244; 564/247
[58] Field of Search ................. 564/229, 244, 247, 80, 564/84, 226; 424/321, 326, 311; 560/139

[56] References Cited

U.S. PATENT DOCUMENTS 3,978,126 8/1976 Panneman .......................... 564/229

FOREIGN PATENT DOCUMENTS 7310741 2/1975 Netherlands .
1475586 6/1977 United Kingdom .

Primary Examiner—Natalie Trousof
Assistant Examiner—L. Hendriksen

Attorney, Agent, or Firm—Abelman, Frayne, Rezac & Schwab

[57] ABSTRACT

The present invention is dealing with compounds of the formula:

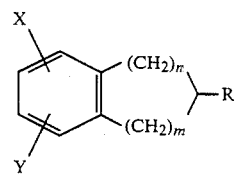

and pharmaceutically acceptable salts thereof, in which n and m represent the number 1 or 2, X and Y hydrogen, alkyl (1–4 C), alkoxy (1–4 C), hydroxy, halogen, hydroxymethyl, trifluoromethyl, acyl (1–4 C), acyloxy (1–4 C) or the group $NR_x R_y$, in which $R_x$ and $R_y$ represent hydrogen, alkyl (1–4 C) or a sulphonyl group and R represents the group

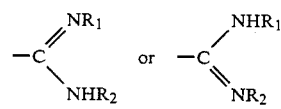

in which $R_1$ and $R_2$ represent hydrogen, alkyl (1–4 C), hydroxy, alkoxy (1–4 C), phenylalkoxy (7–10 C), acyloxy, amino or mono or dialkyl (1–4 C) amino, having potent platelet aggregation inhibiting properties.

6 Claims, No Drawings

CARBOXYIMIDAMIDE DERIVATIVES

This is a continuation of application Ser. No. 214,889, filed Dec. 9, 1980, now abandoned.

The present invention relates to new IH-indene carboximidamide derivatives and higher ring homologs thereof and to a pharmaceutical preparation which contains these new compounds as active constituent.

In British patent specification No. 1,475,586 a description is given of related benzocyclobutene-, indene-, and tetrahydronaphthalene carboximidamide derivates which possess a blood-platelet-aggregation inhibiting activity. Within this series of known compounds the maximum blood platelet aggregation inhibiting activity was found in the benzocyclobutene series; a somewhat lower activity was generally found in the higher homolog series (indene and naphthalene series). However, it turned out that all compounds of this known series which exhibited a relatively strong action in inhibiting blood platelet aggregation at the same time exhibited mutagenic properties, which rendered these compounds absolutely unsuitable for further pharmacological and clinical studies.

In other words in the above group of compounds a relatively potent blood platelet inhibiting activity was always found to be combined with mutagenic properties.

Surprisingly, it is found that compounds having the general formula I:

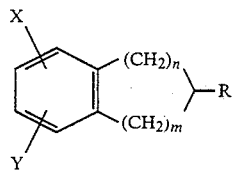

and pharmaceutically acceptable salts thereof, in which n and m represent the number 1 or 2, X and Y hydrogen, alkyl (1-4 C), alkoxy (1-4 C), hydroxy, halogen, hydroxymethyl, trifluoromethyl, acyl (1-4 C), acyloxy (1-4 C) or the group $NR_x R_y$, in which $R_x$ and $R_y$ represent hydrogen, alkyl (1-4 C) or a sulphonyl group and R represents the group

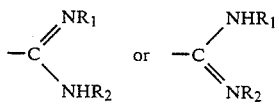

in which $R_1$ and $R_2$ represent hydrogen, alkyl (1-4 C), hydroxy, alkoxy (1-4 C), phenylalkoxy (7-10 C), acyloxy, amino or mono or dialkyl (1-4 C) amino, exhibit potent inhibition of blood platelet aggregation, whereby the mutagenic activity is absent or only very weak. The new compounds furthermore exhibit a positive inotropic effect. The combination of properties, inhibition of blood platelet aggregation and an increase in the contractility of the heart, imparts a unique profile to the new compounds.

The compounds in accordance with general formula I can be prepared in a manner known for analogous compounds. Thus the compounds I can be prepared by condensation of the nitrile II

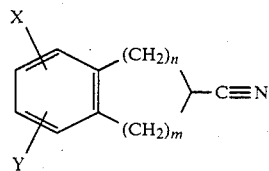

with an amine, hydrazine or hydroxylamine derivative with the general formula III:

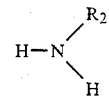

or an acid-addition salt thereof, in which X, Y, $R_2$, m and n have the significance mentioned above.

Furthermore, the compounds I can be prepared by condensation of an O- or S-alkyliso(thio)amide with the general formula:

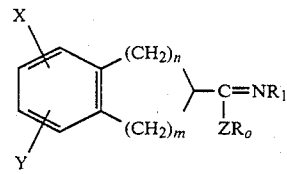

or an acid-addition salt thereof, in which $R_1$, X, Y, m and n have the significance referred to previously, while Z represents an oxygen or sulphur and $R_o$ hydrogen or a lower alkyl group, preferably methyl or ethyl, with an amine, hydrazine or hydroxylamine derivative as per general formula III or an acid-addition salt thereof.

The starting material required for the latter-mentioned synthesis can for example be prepared from the corresponding acid chloride V:

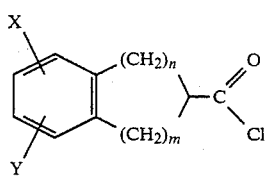

For this purpose the acid chloride is reacted with ammonia or a primary amine into the corresponding primary or secondary amide, after which, if desired, the oxygen atom of the carboxamido group is replaced in a generally known manner by a sulphur atom.

Both the carbothionamide compound and the carboxamide compound (which is obtained previously during the synthesis) can be converted into the starting material IV by alkylation of the sulphur or oxygen atom respectively, e.g. by means of methyl iodide.

The starting material IV can furthermore be prepared very easily from compound II by reaction with, for example, methanol or ethanol in acid or basic environment.

Compounds I can also be directly prepared from the said carbothionamide having the general formula:

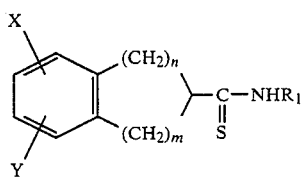

VI in which X, Y, R₁, m and n have the significance referred to above, with an amine, hydrazine or hydroxylamine derivative having the general formula III, or an acid-addition salt thereof.

Amine, hydrazine and hydroxylamine derivatives in accordance with the general formula III, which are used in the above-mentioned condensation reactions, are for example: ammonia ($NH_3$), methylamine, ethylamine, propylamine, isobutylamine, butylamine, hydroxylamine, hydroxylaminemethylether, hydroxylamine-ethylether, hydroxylamine propylether, hydroxylamine benzylether, hydrazine, 1-methylhydrazine, 1,1-dimethylhydrazine, and acid-addition salts thereof.

Preferably most substituents at the phenyl ring (X, Y) or at the nitrogen atoms ($R_1$, $R_2$) present in the end product I are already present in one of the said starting materials.

However it is also quite feasible to modify or to introduce one or several substituents after the said condensation reactions, leading to a compound with formula I.

Thus in a compound I, one of the nitrogen atoms present can be alkylated in a well-known manner, e.g. by means of alkyl-halogenides, by means of an Eschweiler-Clarke reaction, or by acylation followed by reduction.

The optional N-hydroxy group ($R_1$ or $R_2$ is hydroxy) will, during such alkylation, similarly be alkylated. By means, for example, of diazomethane, diazo-ethane or dimethylsulphate, or by means of mild acylation this N-hydroxy group can furthermore be specifically alkylated or acylated.

Acylation of the N-hydroxy group carried out after performing the above-mentioned condensation reactions is even the preferred way of synthesis.

The compounds with formula I have an alkaline character. Dependent on the reaction milieu in which they are prepared, they can be obtained as a free base or as acid-addition salt. If required however the free base I can be prepared from the salt, for example by reaction with an alkaline compound or by means of an ion exchanger, whilst the free base I can be converted in a simple manner into an acid-addition salt.

Pharmaceutically-acceptable acid-addition salts are obtained by reacting the free base I with acids, such as hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid.

From the general formula I for the end products it appears that the compounds in accordance with the invention can contain one asymmetric carbon, as a result of which apart from racemic mixtures I also optically active compounds I are feasible. These optically active compounds I are similarly counted among the compounds in accordance with the invention. They can be prepared directly from an optically active starting product (II, IV, VI) or obtained by resolving the racemate I, in a manner suitable for such splitting, into its optical antipodes.

By the term alkyl (1-4 C) as used in the definitions of X, Y, $R_x$, $R_y$, $R_1$ and $R_2$ is meant a saturated hydrocarbon with 1 to 4 carbon atoms, such as methyl, ethyl, propyl, isopropyl, butyl, isobutyl and tert.butyl.

An alkoxy (1-4 C) group is an alkyloxy group, in which the term alkyl has a similar meaning as above.

By the term "sulphonyl group" is preferably meant an alkyl sulphonyl or aryl sulphonyl group especially a mesyl or tosyl group.

An acyl group with 1-4 carbon atoms, used in the definition of X and Y, is derived from a carboxylic acid with 1 to 4 carbon atoms such as acetic acid, propionic acid of butyric acid. The term acyl in the acyloxy group of the definitions of X and Y has a similar meaning.

By halogen in the definition of X and Y is meant iodine, bromine, chlorine and fluorine. The preferred halogens are chlorine and bromine.

The acyloxy group in the definition of $R_1$ and $R_2$ is derived from an aliphatic, aromatic or araliphatic carboxylic acid with 1 to 10 carbon atoms. Acyloxy groups derived from aliphatic carboxylic acids with 1-6 carbon atoms, such as acetic acid, propionic acid, butyric acid and hexanoic acid, as well as acyloxy groups derived from phenyl- or phenylaliphatic carboxylic acids with 7-10 carbon atoms, such as benzoic acid, phenylacetic acid, phenylpropionic acid, salicylic acid, acetylsalicylic or cinnamic acid are preferred.

The said compounds in accordance with the invention can be administered either orally, locally or parenterally, preferably in a daily dose between 0.01 and 50 mg/kg body weight. For this purpose the compounds are placed in a form suitable for oral, local or parenteral administration, for example a tablet, pill, capsule, solution, suspension, emulsion, paste or spray. A preferred embodiment is a form of administration for oral use.

Compounds which are preferred are compounds of formula I in which n and m are identical (either 1 or 2) and in which R is one of the following structures:

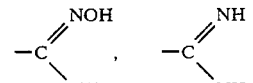

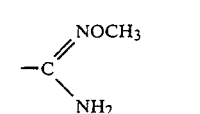

and to a lesser degree:

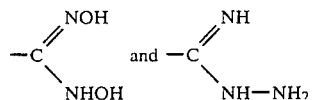

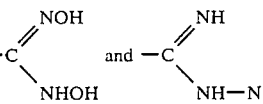

Particular preference is given to compounds I in which R has one of the above-mentioned meanings to be preferred in combination with one or two substituents at the phenyl group.

In case of mono-substitution at the phenyl group preference is given to the meta or para position, and in case of di-substitution the para position in combination with the meta or ortho position is preferred.

Meta/para di-substitution is preferred over mono substitution and other di-substitutions not only from structure-activity considerations, but also—for identical substituents (and n=m)—for synthetic chemical reasons (no racemate).

The phenyl substituent of choice is the alkoxy group, especially the methoxy group. Particular preference is given to the meta/para dimethoxy substitution.

The position of the double bond between the nitrogen and carbon atom in group R of formula I cannot be clearly specified, because equilibrium will prevail between the carboximidamide groups:

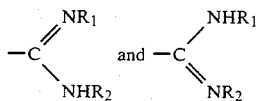

PREPARATION OF THE STARTING MATERIALS

A. Ethyl-2-cyano-1,3-dihydro-5,6-dimethoxy-2H-Indene-2-carboxylate

In a 10 l 3-neck vessel $NaOC_2H_5$ was made up by adding in approximately one hour small pieces of sodium (38.7 g; 1.68 mol) to absolute EtOH (900 ml). The temperature was maintained at 60°–70° C.

After all sodium had reacted, cooling was undertaken to room temperature and then 1650 ml of dry TFH, dried on molecular screen (4Å), and ethylcyanoacetate (190 g, 179 ml, 1.68 mol) were added all at once. After 5 minutes a precipitate starts to form which slowly becomes thicker. After 30 minutes of subsequent stirring cooling was undertaken with ice water down to 10°–15° C. and after this, as rapidly as possible (2 to 3 minutes) a solution of 1,2-bis(bromoethyl)-4,5-dimethoxybenzene (272.2 g, 0.84 mol) in dry THF (1000 ml) was added.

As a result of the exothermic nature of the reaction, the temperature rises to about 35° C. After this cooling down to room temperature was undertaken with subsequent stirring for one hour.

Subsequently the reaction mixture was evaporated as far as possible and the residue was distributed between methylenechloride (750 ml) and water (about 400 ml). The layers were separated and the water layer was then extracted twice with methylenechloride (250 ml). The methylenechloride extracts collected were washed once with water (200 ml) and dried on $NA_2SO_4$. After filtering off the drying agent, the filtrate was evaporated. This gave about 300 g of yellow oil.

300 ml of ether was added to the residue and after inoculation 80.5 g of the substance desired crystallised out. Melting point 109° C. Rf=0.32 on $SiO_2$ in toluene-:ethylacetate (9:1).

B. 2,3-dihydro-5,6-dimethoxy-1H-Indene-2-carbonitrile

The product obtained in A (80 gram, 0.29 mol) was suspended in DMSO (160 ml). To this distilled water (12 ml; 0.67 mol) and iodine-free sodium chloride (5.6 g; 0.096 mol) was added. Then whilst being stirred for about 3 hours the reaction mixture was heated by means of an oil bath to 170° C., until evolution of $CO_2$ had terminated.

After cooling down to room temperature the darker reaction mixture was dropped slowly into distilled water (1000 ml). The precipitate was extracted with methylene chloride (4×200 ml) and the extracts collected, after washing once with distilled water (200 ml) were dried on $Na_2SO_4$ and evaporated. In order to remove individual more-polar byproducts the residue (58.2 g) was filtered over silicagel with toluene-ethyl acetate 98:2 and crystallised by being dissolved in as little acetone as possible and adding a similar volume of hexane. This gave 54 g of pure nitrile.

Rf=0.43 on $SiO_2$ in toluene:ethylacetate (8:2).

EXAMPLE 1

2,3-dihydro-5,6-dimethoxy-N'-hydroxy-1H-Indene-carboximidamide hydrochloride

A. Hydroxylamine solution

A 1.35N hydroxylamine solution was obtained by adding a warm solution of hydroxylamine hydrochloride (56.3 g, 0.81 mol in 325 ml abs. methanol) whilst stirring to a warm $NaOCH_3$ solution (18.6 g sodium, 0.81 mol in 275 ml abs. methanol). The reaction mixture was cooled down to room temperature and after about 15 minutes the NaCl precipitate formed was filtered off.

B. Reaction with nitrile

The hydroxylamine solution A was added to 2,3-dihydro-5,6-dimethoxy-1H-indene-2-carbonitrile (54.2 g, 0.27 mol) and the suspension, whilst being stirred, was heated up to 40° C. After about 30 minutes all nitrile passed into solution and stirring was continued for 15 hours at 40° C., after which a white precipitate had formed. Subsequently 500 ml methanol was evaporated and then about 1 liter of distilled water was added to the concentrate.

The crystal mass was drawn off, washed with water until it became neutral and subsequently washed several times with ether to remove water. After drying to constant weight 70 g of free base was obtained. Melting point: 176° C. (dec).

C. HCl salt

The 70 gram of free base was suspended in 1 liter absolute methanol and, whilst being stirred and possibly cooled, was acidified with a methanolic HCl gas solution (about 66 ml 4.5N) to give pH 3, whereby the base passed into solution. Subsequently, whilst being stirred, 2 liters of dry ether were added and the crystallisate formed, after being cooled for about 1 hour in the cooling cupboard, was filtered off, washed with methanol-ether 1:3 and was dried. This supplied 45 g of the HCl salt.

After recrystallisation from absolute methanol a further 37 gram of pure product was obtained.

Rf=0.35 on $SiO_2$ in methylenechloride:methanol (9:1); melting point 225° C. (dec.).

EXAMPLE 2

In a similar manner the following compounds were prepared by reaction of the corresponding nitrile with hydroxylamine, hydrazine or ammonia;

2,3-dihydro-5,6-dimethoxy-1H-indene-2-carboximide acid hydrazide hydrochloride hydrate, melting point 199° C. (dec.);

2,3-dihydro-N'-hydroxy-1H-indene-2-carboximidamide hydrochloride, melting point 150° C. (dec.);

5,6-dichloro-2,3-dihydro-N'-hydroxy-1H-indene-2-carboximidamide hydrochloride, melting point 223°–225° C. (dec.);

2,3-dihydro-5,N'-dihydroxy-6-methoxy-1H-indene-2-carboximidamide hydrochloride, melting point 216° C. (dec.);

2,3-dihydro-N'-hydroxy-5-methyl-1H-indene-2-carboximidamide hydrochloride, melting point 156° C. (dec.);

2,3-dihydro-5,6-dimethoxy-1H-indene-2-carboximidamide hydrochloride, melting point 210° C. (dec.);

5-fluoro-2,3-dihydro-N'-hydroxy-1H-indene-2-carboximidamide hydrochloride, melting point 144° C.;

2,3-dihydro-N'-hydroxy-4,6-dimethyl-1H-indene-2-carboximidamide hydrochloride, melting point 180° C. (dec.);

2,3-dihydro-N'-hydroxy-4-methoxy-1H-indene-2-carboximidamide hydrochloride; melting point 193° C.;

6,7,8,9-tetrahydro-N'-hydroxy-5H-benzocycloheptene-7-carboximidamide.HCl, melting point 219° C.;

2,3-dihydro-N'-hydroxy-5-methyl-6-methoxy-1H-indene-2-carboximidamide;

2,3-dihydro-N'-hydroxy-5-dimethylamino-1H-indene-2-carboximidamide;

2,3-dihydro-N'-hydroxy-5-tert.butyl-1H-indene-2-carboximidamide;

2,3-dihydro-N'-hydroxy-4,7-dimethoxy-1H-indene-2-carboximidamide;

2,3-dihydro-N'-hydroxy-5-tosylamino-1H-indene-2-carboximidamide;

2,3-dihydro-N'-hydroxy-4,5-dimethoxy-1H-indene-2-carboximidamide;

2,3-dihydro-N'-hydroxy-4,7-dimethyl-1H-indene-2-carboximidamide;

2,3-dihydro-N'-hydroxy-5,6-dimethyl-1H-indene-2-carboximidamide;

2,3-dihydro-N'-hydroxy-4,7-dichloro-1H-indene-2-carboximidamide;

2,3-dihydro-5,6,N'-trihydroxy-1H-indene-2-carboximidamide.

EXAMPLE 3

N'-acetyloxy-2,3-dihydro-5,6-dimethoxy-1H-indene-2-carboximidamide

A suspension of 6.6 g (28 mmol) 2,3-dihydro-N'-hydroxy-5,6-dimethoxy-1H-indene-2-carboximidamide was stirred in 50 ml of acetic acid anhydride for 1 hour at room temperature. The suspension was subsequently poured out into 500 ml of ice water and, after 2 hours stirring, was drawn off and washed to neutral with water.

After drying to constant weight the residue was recrystallised from methylenechloride/methanol (1:1). Yield 5.5 g, melting point 147° C.

The corresponding propionyloxy, butyryloxy and acetylsalicylyloxy derivatives were prepared in an analogous manner.

EXAMPLE 4

2,3-dihydro-5,6-N'-trimethoxy-1H-indene-2-carboximidamide hydrochloride

A. A sodium methanolate solution, which had been prepared by dissolving 3.45 g (150 mmol) sodium in 50 ml of methanol, was added to a solution of 12.5 g (150 mmol) hydroxylamine methylether hydrochloride in 60 ml methanol.

After about 5 minutes stirring the sodium chloride formed was filtered off and the filtrate was added to 10 g (50 mmol) 2,3-dihydro-5,6-dimethoxy-1H-indene-2-carbonitrile.

After 15 hours stirring at 50° C. the methanol was removed and the residue was stirred together with 250 ml water.

After sucking off the precipitate, neutral washing with water and drying to constant weight, the amidoxime was suspended in 35 ml methanol and was acidified with 2N of methanolic HCl solution.

After adding 165 ml ether to the solution, the hydrochloride crystallised out. Yield 11.2 g, melting point 191° C. (dec.).

B. To a solution of 92 mg (4 mmol) sodium in 5 ml ethanol was added one after the other: 0.5 ml water, 0.55 g (2 mmol) 2,3-dihydro-N'-hydroxy-5,6-dimethoxy-1H-indene-2-carboximidamide hydrochloride and, after seventy minutes stirring, 0.3 ml (about 3 mmol) of dimethyl sulphate was added.

After stirring for one hour at room temperature once again 2 mmol sodium ethanolate solution was added together with 0.2 ml (2 mmol) dimethyl sulphate.

After a further one hour stirring at room temperature the solvent was evaporated. The residue was subsequently put into ethylacetate and washed 3 times with water. After drying the organic layer was evaporated to dryness on sodium sulphate and the residue was subsequently converted into the hydrochloric salt by suspension in 3 ml methanol and acidification with 2N methanolic HCl.

The addition of 3 ml ether to the solution caused the hydrochloride to crystallise out. Yield 370 mg; melting point 191° C.

EXAMPLE 5

2,3-dihydro-N,N'-dihydroxy-5,6-dimethoxy-1H-indene-2-carboxamidamide hydrochloride Whilst stirring at 45° C. small portions of about 7.5 mmol of a sodium methanolate solution were added to a suspension of 10 g (50 mmol) 2,3-dihydro-5,6-dimethoxy-1H-indene-2-carbonitrile and 10.5 g (150 mmol) hydroxylamine-hydrochloride in 80 ml methanol. In all, spread over 48 hours, about 40 mmol of sodium methanolate was used.

After cooling down to room temperature 80 ml of ether was added and the precipitate was drawn off. This precipitate was subsequently, so as to remove salts, stirred twice with 50 ml water and was subsequently recrystallised from methanol-ether.

The crystallisate (7.0 g, melting point 149° C.) was then dissolved in methanol and acidified with a 2N methanolic HCl gas solution. The addition of an equal volume of ether caused the HCl salt to crystallise out. Yield 7.9 g, melting point 205° C. (dec.).

EXAMPLE 6

1,2,3,4-tetrahydro-N'-hydroxy-5,6-dimethoxynaphthalene-2-carboximidamide hydrochloride A sodium methanolate solution, which had been made up by dissolving 2.07 g (90 mmol) sodium in 30 ml methanol, was added to a solution of 6.25 g (90 mmol) hydroxylamine-hydrochloride in 37 ml methanol.

After 5 minutes stirring the sodium chloride formed was filtered off and the filtrate was added to 6.54 g (30 mmol) 1,2,3,4-tetrahydro-5,6-dimethoxy-naphthalene-2-carbonitrile.

After heating for 20 hours at 40° C. the methanol was removed and the residue was stirred for about 15 minutes with 200 ml water.

After sucking off the precipitate, neutral washing with water and drying to constant weight, 6.2 g of substance was obtained.

A suspension thereof in 18 ml methanol was acidified with 2N methanolic HCl. During this all the substance passed into solution.

After addition of 55 ml ether, the HCl salt crystallised out. Yield 5.1 g, melting point 222° C. (dec.).

EXAMPLE 7

A.

6,7,8,9-tetrahydro-2,3-dimethoxy-5H-benzocycloheptene-7-carbonitrile 8 g (36.4 mmol) 5,6,8,9-tetrahydro-2,3-dimethoxy-7H-benzocycloheptene-7-on and 7.1 g (36.4 mmol) tosylmethylisocyanide (TOSMIC) was dissolved in 120 ml of dry dimethoxy-ethane.

After cooling down to 0°-5° C., and under nitrogen, a solution of 8 g (73 mmol) potassium-tert.butylate in 240 ml dimethoxy-ethane/tert.butanol (1:1) was dripped in.

After 45 minutes stirring the reaction mixture was brought to room temperature and stirred again for 45 minutes. The subsequent procedure was to pour the reaction mixture into two liters of water and to extract using an ether/methylene chloride mixture.

The organic extracts were washed with water, dried on sodium sulphate and evaporated to dryness.

The crude product was purified by chromatography over a Fertig column (Merck type C) with toluene-/ethyl acetate (9:1) as eluent.

Yield of pure nitrile 6.75 g, melting point 99° C.

B.

6,7,8,9-tetrahydro-N'-hydroxy-2,3-dimethoxy-5H-benzocycloheptene-7-carboximidamide hydrochloride (via imino ethylether)

A solution of 6 g (26 mmol) 6,7,8,9-tetrahydro-2,3-dimethoxy-5H-benzocycloheptene-7-carbonitrile in 22 ml chloroform and 6 ml ethanol was saturated at 0° C. with HCl gas. After 24 hours in the refrigerator the solvents were removed and the imino-ether hydrochloride was dissolved in 100 ml methylene chloride. After treating this solution with a sodium bicarbonate solution, neutral washing was carried out and the solvent was removed.

Rf in CH$_2$Cl$_2$:MeOH (9:1)=0.65 on SiO$_2$.

Subsequently a hydroxylamine solution, which had been prepared by adding a solution of 1.8 g (78 mmol) sodium in 29 ml methanol to 5.4 g (78 mmol) hydroxylamine-hydrochloride in 29 ml methanol was added to the crystalline imino-ether (7.2 g). After stirring for 45 minutes at room temperature the solvent was removed and the residue was stirred with water.

Filtering off of the deposit, neutral washing with water and drying to constant weight supplied 5.9 g of the desired amidoxime.

A suspension of this amidoxime in 30 ml methanol gave, after acidification with 2N methanolic HCl, a solution of the hydrochloride which after concentration to about 20 ml and the addition of 150 ml ether, began to crystallise. Yield 6.55 g, melting point 235° C. (dec.).

EXAMPLE 8

2,3-dihydro-N'-hydroxy-5,6-dimethoxy-N-methyl-1H-indene-2-carboximidamide 23 ml dimethylformamide was added to sodium hydride obtained by removed of the oil with hexane from 1440 mg of a 60% dispersion of sodium hydride in oil (36 mmol sodium hydride) and after which 2.5 g (36 mmol) hydroxylamine-hydrochloride was added. After 20 minutes stirring the deposit was filtered off and the filtrate was added to 7.07 g (18 mmol) methyl-2,3-dihydro-5,6-dimethoxy-N-methyl-iH-indene-2-carboximidothioate hydro-iodide.

The reaction mixture was stirred for 45 minutes at room temperature, and subsequently poured into 600 ml water. The pH of the mixture was adjusted to pH=9 using 4N sodium hydroxide, after which the deposit formed was drawn off and washed till neutral. Drying to constant weight gave 4.0 g of the title compound.

Rf in CH$_2$Cl$_2$:MeOH (9:1)=0.35 on SiO$_2$.

EXAMPLE 9

2,3-dihydro-5,6-dimethoxy-1H-indene-2-carboximide acid hydrazide hydrochloride hydrate In a manner similar to that described in example 7B, ethyl-2,3-dihydro-5,6-dimethoxy-1H-indene-2-carboximidate was dissolved in a 5-fold excess of ethanol, and after this, during stirring, one equivalent hydrazine was added. The product obtained was processed in the same way as in example 7B and recrystallised from aqueous THF. Melting point 199° C. (dec.).

In a corresponding manner were prepared:

2,3-dihydro-5,6-dimethoxy-1H-indene-2-carboximidamide. HCl, melting point 210°-212° C. (reagent: ammonium-chloride)

2,3-dihydro-5,6-dimethoxy-N-butyl-2-carboximidamide, (reagent: butylamine).

I claim:

1. Carboximidamide derivatives of the general formula:

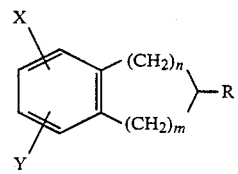

in which n and m represent the value 1 or 2, X and Y hydrogen, alkyl (1-4 C), alkoxy (1-4 C), hydroxy, halogen, hydroxymethyl, trifluoromethyl, acyl (1-4 C), acyloxy (1-4 C) or the group NR$_x$R$_y$, in which R$_x$ and R$_y$ represent hydrogen, alkyl (1-4 C) or a sulphonyl group and R represents the group:

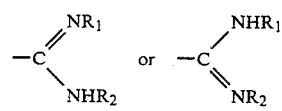

in which R$_1$ and R$_2$ represent hydrogen, alkyl (1-4 C), hydroxy, alkoxy (1-4 C), phenylalkoxy (7-10 C), acyloxy, amino or mono- or dialkyl (1-4 C)-amino, or a pharmaceutically acceptable salt thereof.

2. A compound according to claim 1 of the formula:

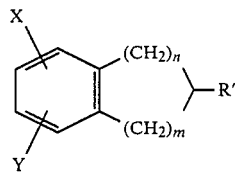

in which X and Y have the meanings indicated in claim 1, m and n have both the value 1 or the value 2 and $R^1$ is selected from

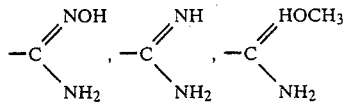

or a pharmaceutically acceptable salt thereof.

3. A compound according to claim 2, in which one of the symbols X and Y or both have a meaning other than hydrogen.

4. A compound according to claim 3 in which one or both of the symbols X and Y represent an alkoxy group.

5. Compound in accordance with claim 1 having the formula:

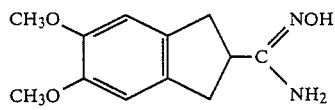

or a pharmaceutically-acceptable salt thereof.

6. A pharmaceutical composition for use as a blood platelet aggregation inhibitor which comprises, as active ingredient, a blood platelet aggregation inhibiting amount of a compound as defined in claim 1, or a pharmaceutically acceptable salt thereof, in a pharmaceutically acceptable carrier.

* * * * *